United States Patent
Pitt et al.

(10) Patent No.: US 8,999,295 B2
(45) Date of Patent: Apr. 7, 2015

(54) TECHNIQUE FOR DRUG AND GENE DELIVERY TO THE CELL CYTOSOL

(75) Inventors: William G. Pitt, Orem, UT (US); Ghaleb Husseini, Provo, UT (US)

(73) Assignee: Brigham Young University, Provo, UT (US)

( * ) Notice: Subject to any disclaimer, the term of this patent is extended or adjusted under 35 U.S.C. 154(b) by 227 days.

(21) Appl. No.: 12/940,047

(22) Filed: Nov. 5, 2010

(65) Prior Publication Data

US 2011/0104258 A1 May 5, 2011

Related U.S. Application Data

(60) Provisional application No. 61/280,560, filed on Nov. 5, 2009.

(51) Int. Cl.
| | |
|---|---|
| *A61B 8/00* | (2006.01) |
| *A61K 9/127* | (2006.01) |
| *A61K 47/06* | (2006.01) |
| *A61K 9/107* | (2006.01) |
| *A61K 31/7105* | (2006.01) |
| *A61K 47/48* | (2006.01) |

(52) U.S. Cl.
CPC ............... *A61K 47/06* (2013.01); *A61K 9/1075* (2013.01); *A61K 9/1271* (2013.01); *A61K 9/1277* (2013.01); *A61K 31/7105* (2013.01); *A61K 47/48815* (2013.01); *Y10S 977/773* (2013.01); *Y10S 977/907* (2013.01)

(58) Field of Classification Search
None
See application file for complete search history.

(56) References Cited

U.S. PATENT DOCUMENTS 6,433,898 B1 *  8/2002  Bestmann ...................... 358/518
6,443,898 B1 *  9/2002  Unger et al. .................. 600/458

OTHER PUBLICATIONS

Lattin, et al. (2012) "Formation of eLiposomes as delivery vehicle", Colloids and Surfaces B: Biointerfaces, 89: 93-100.*
Couture et al., (2006) "Investigating perfluorohexane particles with high-frequency ultrasound," Ultrasound in Medicine and Biology, 32, 73-82.
Giesecke and Hynynen (2003) "Ultrasound-mediated cavitation thresholds of liquid perfluorocarbon droplets in vitro," Ultrasound in Medicine and Biology, 29, 1359-1365.
Kisak, et al., (2004) "The vesosome—A multicompartment drug delivery vehicle," Current Medicinal Chemistry, 11, 199-219.
Miller and Song (2002) "Lithotripter shock waves with cavitation nucleation agents produce tumor growth reduction and gene transfer in vivo," Ultrasound in Medicine and Biology, 28, 1343-1348.
Rapoport, et al., (2007) "Multifunctional nanoparticles for combining ultrasonic tumor imaging and targeted chemotherapy," Journal of the National Cancer Institute, 99, 1095-1106.
Soman et al., (2006) "Acoustic activation of targeted liquid perfluorocarbon nanoparticles does not compromise endothelial integrity," IEEE Transactions on Nanobioscience, 5, 69-75.

* cited by examiner

*Primary Examiner* — Robert M Kelly
(74) *Attorney, Agent, or Firm* — Kunzler Law Group

(57) ABSTRACT

Provided herein is a composition, a method, and a system for delivering a functional molecule to the cytosol of a cell, comprising a liposome configured to be taken into a cell, including by a process selected from the group consisting of endocytosis, pinocytosis or phagocytosis, the liposome comprising a phase transforming liquid with vapor pressure capable of forming a gas at low pressure, said liquid being associated with the liposome, and the liposome further comprising at least one functional molecule selected from the group consisting of a therapeutic molecule, a detectable label, and a targeting molecule.

20 Claims, 4 Drawing Sheets

TECHNIQUE FOR DRUG AND GENE DELIVERY TO THE CELL CYTOSOL

CROSS-REFERENCES TO RELATED APPLICATIONS

This application claims priority to U.S. Provisional Patent Application No. 61/280,560 entitled "Technique for Drug and Gene Delivery to the Cell Cytosol" and filed on 5 Nov. 2009 for William G. Pitt, which is incorporated herein by reference.

FIELD OF THE INVENTION

The technology provided herein relates to drug and gene delivery and more particularly relates to selective drug and gene delivery via endocytosis.

BACKGROUND

Cells ingest foreign molecules through the process of endocytosis, in which the foreign material is taken into the endosome and then digested before being released into the cell. The activity of therapeutic molecules may depend on their release from the endosome before digestion. Techniques used to rupture endosomes include bursting through osmotic swelling, bursting through photodynamic radiation, bursting by the thermal swelling of a polymer, bursting through the phase change of a polymer (coil to rod transformation), destabilization of endosomal membrane by surfactants carried into the endosome with the drug or gene.

SUMMARY

Reference throughout this specification to features or similar language does not imply that all of the features that may be realized with the present invention should be or are in any single embodiment of the invention. Rather, language referring to the features is understood to mean that a specific feature or characteristic described in connection with an embodiment is included in at least one embodiment of the present invention. Thus, discussion of the features and characteristics, and similar language, throughout this specification may, but do not necessarily, refer to the same embodiment.

Furthermore, the described features, and characteristics of the invention may be combined in any suitable manner in one or more embodiments. One skilled in the relevant art will recognize that the invention can be practiced without one or more of the specific features or characteristics of a particular embodiment. In other instances, additional features and characteristics may be recognized in certain embodiments that may not be present in all embodiments of the invention.

The features and characteristics of the present invention will become more fully apparent from the following description and appended claims, or may be learned by the practice of the invention as set forth hereinafter.

Provided herein is a composition comprising a liposome configured to be taken into a cell, a phase transforming liquid associated with the liposome and having a vapor pressure capable of forming a gas at low pressure, said associated with the liposome, and at least one functional molecule such as a therapeutic molecule, a detectable molecule, or, a targeting molecule. In some embodiments the liposome is configured to be taken into the cell by a process including without limitation endocytosis, pinocytosis or phagocytosis. The liposome sometimes comprises non-toxic amphipathic molecules containing at least one hydrophilic moiety and one hydrophobic moiety. The amphipathic molecules may be selected from the group consisting of cholesterols, phosphoglycerides, phospholipids, glycolipids, sphingomyelins, synthetic amphipathic molecules and polymeric molecules, and derivatives thereof, including PEGylated derivatives. In certain embodiments the liposome is from about 50 to about 1,000 nanometers in diameter.

Further provided herein is a composition wherein the phase transforming liquid comprises a nanoemulsion with at least one nanoemulsion droplet. In some embodiments the nanoemulsion droplet is from about 5 nm to about 900 nm in size. The phase transforming liquid is sometimes contained within the liposome. In certain embodiments the phase transforming liquid is in the form of a nanoemulsion droplet attached to the exterior of the liposome by an attachment method including without limitation electrostatic attraction, non-covalent interaction, covalent interaction, hydrophobic interactions, dispersion interactions, and hydrogen bonding interactions. In some embodiments the phase transforming liquid is embedded in the liposomal bilayer. In certain embodiments the phase transforming liquid is an organic liquid. The phase transforming liquid is sometimes an inorganic liquid. In some embodiments the phase transforming liquid is non-toxic.

Featured herein is a phase transforming liquid containing at least one organic or inorganic molecule that forms a gas at low pressure. In certain embodiments the phase transforming liquid is a hydrocarbon that transforms to gas a low pressure. In some embodiments the phase transforming liquid contains at least one fluorocarbon molecule with a normal boiling temperature between $-5°$ C. and $105°$ C. The phase transforming liquid as provided may contain at least one hydrofluorocarbon molecule with a normal boiling temperature between $-5°$ C. and $105°$ C. The phase transforming liquid sometimes transforms to a gas upon decrease in pressure with a volume expansion of at least 10 fold. In certain embodiments the phase transforming liquid transforms to a gas upon decrease in pressure with a volume expansion of from about 10 fold to at least about 1,000 fold.

Herein provided is a composition wherein the phase transforming liquid is in the form of an emulsion stabilized by at least one amphipathic molecule including without limitation naturally occurring amphipathic molecules, synthetic amphipathic molecules, synthetic derivatives of naturally occurring amphipathic molecules, and polymeric molecules.

In certain embodiments of the technology the targeting molecule provided is attached to the liposome by polyethyleneglycol (PEG) spacer chains to molecules incorporated into the liposomal bilayer. In some embodiments the targeting molecule is a biomolecule or a fragment of a biomolecule including without limitation proteins, polypeptides, antibodies, poly nucleic acids, DNA, RNA, carbohydrates, biotin, avidin and vitamins. The targeting molecule is sometimes at least a fragment of an antibody. In some embodiments of the composition the targeting molecule is a folate molecule.

Also provided herein is a composition in wherein the therapeutic molecule is contained within the liposome. The therapeutic molecule may selected from chemotherapeutic drugs, pain relieving drugs, anti-inflammatory drugs, anti-arthritic drugs, hormones, steroids, DNA, RNA, siRNA, poly nucleic acids, toxic molecules, cell signaling molecules, proteins, enzymes and membrane permeabilizing molecules.

In some embodiments the labeling molecule is selected from the group consisting of fluorescent molecules, light absorbing molecules, proteins and enzymes. In certain embodiments the labeling molecule participates in a chemical reaction Herein provided is a method for treating a disease condition in an animal or human comprising providing a liposome comprising a pressure sensitive phase transforming liquid and at least one of a targeting molecule, a therapeutic molecule and a labeling molecule, administering the liposome such that the liposome may be endocytosed by an animal cell and reducing the pressure on the cell such that the phase transforming liquid transforms to a gas with an associated expansion in volume sufficient to rupture the liposome and release into the interior of the endosome the at least one molecule associated with the liposome. In some embodiments the method further comprises reducing the pressure on the cell such that the phase transforming liquid transforms to a gas with an associated expansion in volume sufficient to rupture the endosome and release into the cytosol of the cell the at least one molecule associated with the liposome. In certain embodiments of the method the low pressure generating method is one or more of a static vacuum, oscillatory pressure waves, shock waves, unfocused ultrasound, and focused ultrasound.

Herein provided is a method according to the disclosed technology, wherein the liposome is administered by a tablet, syrup, bolus, implant, injection, lavage, irrigation, enema, suppository, inhalant, nasal spray, eye drop, ear drop, and topical ointment.

Further provided is a method for treating a cell in a cell culture, the method comprising providing a liposome comprising a pressure sensitive phase transforming liquid and at least one of a targeting molecule, a therapeutic molecule and a labeling molecule, administering the liposome such that the liposome may be endocytosed by an animal cell and reducing the pressure on the cell such that the phase transforming liquid transforms to a gas with an associated expansion in volume sufficient to rupture the liposome and release into the interior of the endosome the at least one molecule associated with the liposome. In some embodiments the method further comprises reducing the pressure on the cell such that the phase transforming liquid transforms to a gas with an associated expansion in volume sufficient to rupture the endosome and release into the cytosol of the cell the at least one molecule associated with the liposome. The low pressure generating method may be selected from the group comprising a static vacuum, oscillatory pressure waves, shock waves, unfocused ultrasound, and focused ultrasound.

Herein provided is a system for administering a molecule to a cell cytosol, the system comprising a target cell, a liposome comprising a pressure sensitive phase transforming liquid, and at least one of a targeting molecule, a therapeutic molecule and a labeling molecule, a means to administer the liposome to the endosome of the target cell, and an activating modality configured to generate low pressure sufficient to transform the phase transforming liquid to a gas with volume expansion sufficient to rupture the cell endosome. In some embodiments of the system the cell is in culture. In certain embodiments the cell is in an organism. The organism may be a human in need of treatment.

DETAILED DESCRIPTION OF THE INVENTION

Introduction

Figure 1:
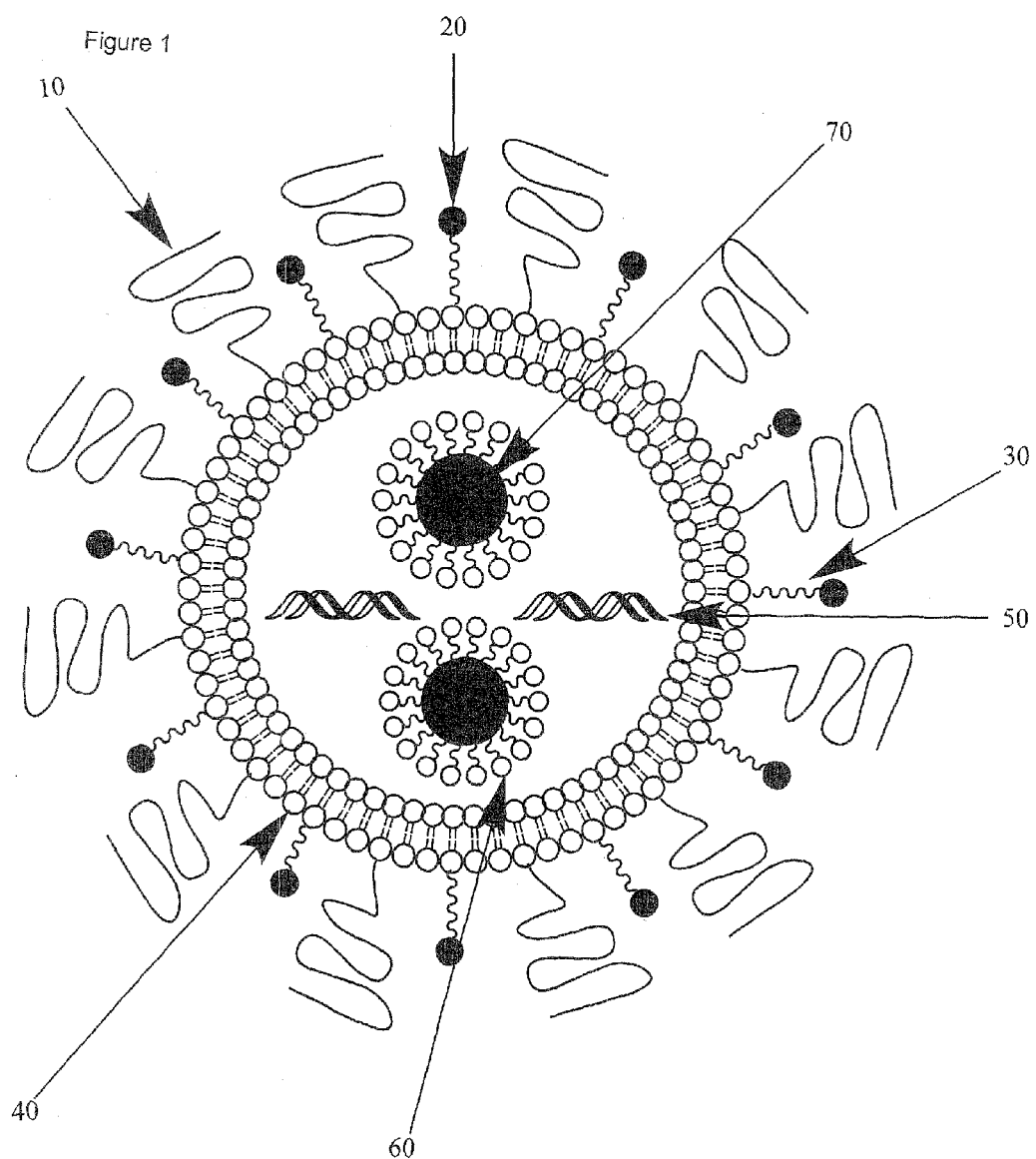
FIG. 1 depicts an illustration of a certain embodiment of the present invention. In this illustration a liposome has a bilayer of phospholipid [40] surrounding a cavity containing a DNA therapeutic [50] and two nanoemulsion droplets of perfluorocarbon liquid [70]. The perfluorocarbon nanoemulsions are surrounded by stabilizing amphipathic molecules [60]. Attached to some phospholipids on the exterior surface of the liposome are PEG chains [10] that confer stealth character to the liposome. Attached to some other phospholipids are PEG chains [30] that are capped with a targeting molecule [20].

Provided herein is a composition, method, and system for delivering agents including drugs, nucleic acids, and proteins to the cell endosome and cytosol by uptake of liposomes into endosomes followed by controlled rupture of liposomes and endosomes to spill the contents into the internal liquid volume of the cell called the cytosol.

The intracellular delivery of drugs and genetic material (DNA or RNA) is normally hampered by the integrity of the cell membrane, which inhibits passive transport into the cell. Pinocytosis, endocytosis and phagocytosis provide a possible pathway into the cell; but there is a stable membrane surrounding pinosomes, endosomes and phagosomes that normally sequesters their content until combination with a primary lysosome and subsequent digestion or inactivation of therapeutic payload. Liposomes may be taken into a cellular compartment called the endosome where the contents of the endosome are "digested" and then usually excreted from the cell. Thus, drugs and genes that are taken into the cell by endosomal uptake are not delivered intact to the cell cytosol.

Herein provided are liposomes that may sequester a nanoemulsion of perfluorocarbon liquid along with a payload of drugs, nucleic acids, or proteins. A nanosized (submicron) vesicle is created that can be endocytosed, that carries a therapeutic (such as a drug or DNA/RNA), and that can break out of the endosome on demand by application of low pressure. The nanoemulsion droplets can be transformed to gas by the application of lowered pressure, sometimes accomplished by ultrasound.

This technology employs a phase changing liquid which will expand at least 10-fold and in some embodiments up to 1,000 fold by volume upon transformation to a gas, and which expansion may break lipid membranes, such as those of the drug carrying liposome or of the endosome, or both, and spill the therapeutic into the cytosol of the cell. A phase change from a nanodroplet of perfluorocarbon liquid to gas produces for example a 250-fold increase in volume that will burst the liposome membrane, spilling the contents into the endosome.

A phase transformation of only 5 nanoemulsion droplets in liposomes in an endosome may rupture the endosome at the same time as the liposomal rupture, thus spilling the liposome contents (including the therapeutic payload) into the cell cytosol with only minimal exposure of the payload to the degradative environment inside the endosome.

In some embodiments in vivo cell transfection delivers drugs and genes to in vivo tumors that display the enhanced permeation and retention (EPR) effect via leaky capillaries. In certain embodiments rupturable liposomes in the circulatory system provide local delivery of analgesics or steroids.

In certain embodiments, a nano-sized vesicle of perfluorocarbon (PFC) liquid is associated with the liposome that contains the drugs or genes. The PFC may be contained inside the liposome, within the liposome membrane, attached to the exterior of the liposome, or closely associated with the liposome in some fashion. After the liposome and associated PFC vesicle is endocytosed, low pressure may be applied to the cell, which causes a phase transformation of the PFC liquid to a gas and ruptures the liposome. The endosome may also succumb to rupture by the expansion.

In certain embodiments ultrasound is used to apply low pressure to the cell. Ultrasound consists of pressure waves of alternating low and high amplitudes. During the low pressure phase of the ultrasound cycle, the pressure can be sufficiently low to transform the emulsion liquid to gas. The ultrasound that causes disruption may be focused on specific tissues in the body, so that only selected tissues will receive the therapeutic compounds. The requisite very short bursts of ultrasound are anticipated to cause no or negligible damage to tissues.

Thus, cells may be treated therapeutically by drugs or genes that are normally excluded from the cell by the cell membrane. In various embodiments treatment may be performed by, for non-limiting example, chemotherapy, antibiotic treatment, pain treatment, hormone therapy, and gene therapy. The composition, method, and system disclosed herein may sometimes be applied to cells in vitro for tissue engineering, cell research and diagnostic applications. Various embodiments include different ways to induce low pressure, variations on the type of surfactant used in the emulsion, the type of liquid used in the emulsion, the types of surfactants used in the liposomes, the manner of encapsulating within or attaching to the liposomes, and the manner of applying ultrasound, including the frequency, pulsing, and amplitude.

Definitions

Endocytosis

The term "endocytosis" as used herein means the cellular process by which the cell engulfs some of its extracellular fluid including material dissolved or suspended in it. A portion of the plasma membrane is invaginated and pinched off forming a membrane-bounded vesicle called an endosome. Most cells continually endocytose external fluid by invaginating their cell membrane and pinching off a vesicle that is then transported and processed within the cell. Lipids and membrane proteins that were incorporated into the endosome are often sorted and returned from the endosome to the cell membrane. Over time, endosomes create an increasingly acidic pH in their lumen by pumping in H+ ions. Many of these endosomes eventually fuse with primary lysosomes to form secondary lysosomes in which the contents of the original endosome are subjected to low pH and degradative enzymes.

Endocytosis is widely used by animal cells because many substances vital to them are large polar molecules that cannot pass through the hydrophobic plasma or cell membrane. Thus, endocytosis is involved multiple functions that are essential to the cell. For example, endocytosis regulates many processes, including nutrient uptake, cell adhesion and migration, receptor signaling, pathogen entry, neurotransmission, receptor downregulation, antigen presentation, cell polarity, mitosis, growth and differentiation, and drug delivery.

Liposome

The term "liposome" as used herein means an artificially prepared vesicle made of lipid bilayer. There are three types of liposomes—MLV (multilamellar vesicles) SUV (Small Unilamellar Vesicles) and LUV (Large Unilamellar Vesicles). A liposome may be composed of naturally-derived phospholipids sometimes mixed with other amphipathic molecules such as cholesterols, phosphoglycerides, glycolipids, and sphingomyelins. The name liposome is derived from two Greek words: 'Lipos' meaning fat and 'Soma' meaning body.

A liposome can be formed at a variety of sizes as unilamellar or multilamellar construction, and its name relates to its structural building blocks, phospholipids. Liposomes may be used for drug delivery due to their unique properties. A liposome encapsulates a volume of aqueous solution inside a hydrophobic membrane. Making liposomes in a solution of DNA or drugs can load the interior of the liposome with the solution. Dissolved hydrophilic solutes cannot readily pass through the lipids. Hydrophobic drugs or therapeutic chemicals can be dissolved into the membrane, and in this way liposome can carry both hydrophobic molecules and hydrophilic molecules.

The liposome lipid bilayer may fuse with other bilayers such as the cell membrane, thus delivering the liposome contents to the cell. Another strategy for liposome drug delivery is to target endocytosis events. Liposomes can be made in a particular size range that makes them viable targets for natural macrophage phagocytosis. These liposomes may be digested while in the macrophage's phagosome, thus releasing its drug. Liposomes can also be decorated with opsonins and ligands to activate endocytosis in other cell types. Thus agents which would normally be unable to diffuse through the membrane can be delivered past the lipid bilayer into the endosome.

Liposomes may have their membranes decorated with molecules that mask them from detection by scavenging cells within the natural immune system. Polyethyleneglycol (PEG) is often attached to phospholipids inserted into a liposome bilayer to endow stealth characteristic to the liposome and thus allow prolonged circulation within the circulatory system of the body. Furthermore, targeting molecules may be attached to the distal terminus of the PEG chains that allow the liposome to attach to certain receptor molecules on the cell surface, which in some cases initiates the endocytosis process.

Formation of liposomes is not a spontaneous process. Lipid vesicles are formed when phospholipids such as lecithin are placed in water, saline or buffer and consequently form one bilayer or a series of bilayers, each separated by water molecules, once enough energy is supplied.

Nanoemulsion

The term "nanoemulsion" as used herein means a suspension of submicron-sized volumes of non-aqueous liquid within an aqueous fluid. The fluid may be a phase transforming liquid as described below. In some embodiments the size of the emulsion droplet is less than 1,000 nm and greater than 5 nm. The size of the emulsion droplet may be between 500 nm and 5 nm. In certain embodiments the size of the emulsion droplet is between 200 nm and 5 nm. For example, the size of the emulsion droplets may be 5 nm, 10 nm, 20 nm, 30 nm, 40 nm, 50 nm, 60 nm, 70 nm, 80 nm, 90 nm, 100 nm, 110 nm, 120 nm, 130 nm, 140 nm, 50 nm, 160 nm, 170 nm, 180 nm, 190 nm, 200 nm, 220 nm, 240 nm, 260 nm, 280 nm, 300 nm, 325 nm, 350 nm, 375 nm, 400 nm, 450 nm, or 500 nm, or any size within these ranges.

The placement of the emulsion droplets may be within the liposome carrying therapeutic substance. The placement of the emulsion droplets may sometimes be outside of the liposome carrying therapeutic substance. In some embodiments the emulsion droplets are attached to the exterior surface of the liposome carrying the therapeutic substance. In certain embodiments the attachment of the emulsion droplets to the liposome may be by electrostatic interactions. The attachment of the emulsion droplets to the liposome is sometimes by covalent interactions. The attachment of the emulsion droplets to the liposome may be by hydrophobic or dispersion interaction. In some embodiments the attachment of the emulsion droplets to the liposome is by hydrogen bonding interactions.

Phase Transforming Liquid

The term "phase transforming liquid" as used herein means a fluid that transforms to a gas upon reduction in, pressure with an attendant increase in volume. The fluid may be a low boiling point liquid that boils near body temperature. It may be any type of organic or inorganic liquid, such as a hydrocarbon, a hydrofluorocarbon, a perfluorocarbon, or other liquid that is not toxic. Perfluorocarbons are not toxic and do not dissolve easily in water. The perfluorocarbons perfluoroheptane, perfluorohexane and perfluoropentane have low boiling points. Perfluoropentane (PFC5) and perfluorohexane (PFC6) have the boiling points closest to body temperature (37° C.).

A phase transforming liquid may have a vapor pressure at body temperature that is greater than the ambient pressure, such that the liquid can form a metastable liquid at body temperature that can transform irreversibly into a gas upon a decrease in the surrounding pressure. An example of such a liquid is perfluoropentane. In certain embodiments a liquid has a vapor pressure at body temperature that is less than the ambient pressure, such that the liquid can form a stable liquid that can transform reversibly into a gas when the local pressure is decreased below the vapor pressure, and then reform into a liquid when the pressure is increased above its vapor pressure. A non-limiting example of such a liquid is perfluorohexane.

A phase transforming liquid may transform into a gas with an expansion in its volume when the pressure is decreased. In certain embodiments a phase transforming liquid transforms into a gas with an expansion in its volume of at least 10, 20, 30, 40, 50, 60, 70, 80, 90, 100, 110, 1120, 150, 200, 300, 400, 500, 600, 700, 800, 900, or 1000 fold. Such expansions can be predicted from known chemical properties, temperature and pressure by those skilled in the relevant art.

A phase transforming liquid may be contained within a liposome or may decorate the outside of the liposome as nanoemulsion droplets. In certain embodiments the phase transforming liquid is not formed into liquid emulsion droplets. The phase transforming liquid sometimes exists as small droplets or blebs within the bilayer membrane forming the boundary of the liposome.

Activating Modality

The term "activating modality" as used herein means method to generate low pressure. In some embodiments low pressure results from applying static vacuum. Low pressure is sometimes generated from oscillatory pressure waves. Low pressure may be generated from focused or unfocused ultrasound.

Targeting Molecule

The term "targeting molecule" as used herein means a molecule with affinity for another molecule, for example a biomolecule on the surface of a specific cell. In active targeting, a specific molecule is attached to the exterior of the liposome or the exterior of the emulsion vesicle if that vesicle is external to the liposome. The specific molecule has a binding interaction with something on the surface of the cells of the targeted tissue. Examples include antibodies on the liposome for some antigen expressed on a cancerous tissue. Another example is the attachment of a folate molecule to the liposome, which is attracted to folate receptors that are overexpressed on the surface of many types of cancer cells. Once the liposome-emulsion complex is injected into the circulatory system, it floats around until it encounters the targeted tissue, upon which it binds to the tissue.

In passive targeting there are no specific ligands or receptors on the liposome-emulsion complex. Instead the complex disperses until it passively collects at a desired tissue. Examples include collection and concentration in the liver or spleen, which organs contain cells that naturally collect particles in the blood. Cancerous tissue often have unorganized and partially developed capillaries that contain holes and fenestrations through which blood born particles can pass through and collect in the tissue beyond. This is commonly called enhanced permeation and retention (EPR), and is employed for passive targeting of cancerous tissues.

A combination of active and passive targeting can also be employed in some embodiments. For example liposomes containing targeting molecules can passively circulate until they leak from the capillaries into tumor tissue displaying the EPR effect. Once extravasated the targeting moieties will actively attach to specific cancer cells within the tissue.

eLiposome

The term "eLiposome" as used herein refers to a liposome that contains at least one nanoemulsion droplet within its aqueous interior. The formation of an eLiposome is one embodiment as provided herein.

Labeling Molecule

A labeling molecule is a molecule whose purpose is to identify the liposome, the location of the liposome within or external to a cell, or the release of liposome contents within an endosome or to the cytosol. Labeling molecules can be fluorescent molecules, or fluorescent molecules attached to biomolecules, such as to phospholipids, drugs, and nucleic acids or attached to emulsions. The fluorescent molecules may change their emission according to their environment such as pH or redox potential. Such molecules are useful in determining drug delivery mechanisms or cell response mechanisms. Labeling molecules may be enzymes that when released to the endosome or cytosol produce a chemical reaction that can be monitored to assess the extent of enzyme release or to assess biological function or processes within the cell. The labeling molecule may be a chemical that is a substrate for a chemical reaction that when released to the endosome or cytosol is transformed in a manner that can be monitored to assess the extent of chemical release or to assess biological function or processes within the cell.

Perfluorocarbon Nanoemulsions

Emulsions are two phase mixtures of water and non-water-soluble liquids in which the non-aqueous phase consists of liquid droplets less than 100 microns in diameter. Many emulsions must be stabilized by some type of surfactant to retain their small size distribution. Perfluorocarbons are not soluble in water and have a carbon structure as in hydrocarbons, but with fluorine atoms in place of all hydrogens. They are inert in the body, and are known for their ability to carry large amounts of oxygen. As emulsions, they are used as oxygen carriers in synthetic blood substitutes. Because perfluorocarbons have no hydrogen atoms, they have minimal interaction with hydrocarbons, and thus do not as readily dissolve lipids or dissolve into lipid membranes, as do hydrocarbons. Compared with oxygen ($O_2$), which has solubility in water of 1.32 mol/m$^3$, perfluoropropane (the gas used clinically in ultrasound contrast agents) has a solubility of 0.19 mol/m$^3$, and perfluorohexane (one of our emulsion liquids) has a solubility of $2.7 \times 10^{-4}$ mol/m$^3$, 4 orders of magnitude less than oxygen solubility.

Some perfluorocarbons have boiling points just above room temperature. Thus they easily boil, or change to a gas when the temperature is increased. Likewise, these same perfluorocarbon liquids can boil into a gas when the surrounding pressure is decreased at a constant temperature. A nanoemulsion of perfluorocarbon exposed to an ultrasonic wave may boil when the local pressure of the wave decreases below the vapor pressure of that liquid at body temperature. For, example, perfluorohexane (PFC6) boils at 57° C., which means that at this temperature, its vapor pressure is 1 atm (0.101 MPa). But at body temperature it has a vapor pressure of 0.48 atm. Thus a static gauge pressure of negative 0.52 atm (−0.525 MPa) or an ultrasonic peak negative pressure of 0.52 atm ($P^-$=0.0525 MPa) may be sufficient to commence boiling the PFC6. Initially as the local pressure of the ultrasonic wave decreases below the vapor pressure of the emulsion droplet, the gas forms; when the oscillating pressure wave reverses and increases in pressure, the gas condenses back into PFC liquid. However, during that short time of gas formation, a large volume expansion occurs. If this emulsion droplet were inside a liposome during expansion, the increased volume may burst the liposome and spill its contents. If several emulsions particles were in a liposome that was inside an endosome, the volume may expand sufficiently to burst the endosome, thus spilling the contents of the liposome into the cytosol.

While perfluoropentane (PFC5) has a normal boiling point of 29° C. it may remain a superheated liquid in submicron emulsion droplets, where the Laplace pressure (excess surface pressure from the high curvature of the nanodroplet) prevents the PFC5 from boiling at 37°. However, this state is metastable, and sufficiently negative pressures in ultrasound will cause the submicron emulsion droplets to expand into and remain a gas at body temperature.

Perfluorocarbon (PFC) nanoemulsions may be made including by subjecting water, surfactants and PFC liquids to very high shear conditions. Mechanical shearing can be employed, such as in a shaker, blender or homogenizer. Some investigators use a low-frequency (20 kHz) ultrasonic probe to create high shear around the probe tip and the cavitating bubbles. In this technique ambient gas (air) may become entrained in the emulsion, or the ultrasound itself may cause the PFC to boil, again forming gas bubbles. PFC emulsion droplets are denser that water, so separation of the emulsion from entrained gas bubbles may be done in a subsequent step by settling or centrifugation. PFC nanoemulsions can be stabilized by fluorocarbon surfactants, phospholipids, proteins, hydrocarbon surfactants, or polymeric surfactants.

Making Nanoemulsions

Nanoemulsions may be made by techniques known in the art. One method is to dissolve the stabilizing surfactant or lipid in chloroform or another solvent and then dry this onto the inside of a glass vial or test tube. Then the non-aqueous phase-changing liquid (such as PFC6) and the water phase can be added. The container is stirred vigorously for several minutes with high shearing to remove the surfactant from the container surface and mix it well into the dispersion of the non-aqueous phase. If the surfactant is a liquid, it can be added directly to the other two components and then mixed. Surfactants include hydrocarbons and perfluorocarbons with polar groups. Additional examples include perfluoroalkyl acids and alcohols, such as perfluorooctanoic acid. PEGylated perfluorocarbons may stabilize the emulsion efficiently, as may phospholipids, glycolipids, phosphoglycerides and sphingomyelins. These latter molecules are featured in some embodiments because they are naturally occurring surfactants found in the body. Mixing and shearing can by done by an ultrasonic probe, or by blending with a high-speed impellor, or by other commonly known techniques. More vigorous shearing leads to smaller particles. Also as the ratio of surfactant to non-aqueous phase increases, the nanoemulsion average particle size is generally smaller. Care should be taken to eliminate gas bubbles from nanoemulsions, such as by using degassed water, etc. Functionalized nanoemulsions can be made by using lipids or surfactants that are covalently bonded on their polar side to special functional molecules. For example, special functional molecules can be attached to the —OH of diglycerides, the phosphate of phospholipids, the nitrogen of phosphatidyl cholines, the —OH of phosphatidyl serines, etc.

Producing eLiposomes eLiposomes can be produce by at least 2 different laboratory techniques. The first technique is similar to the production of a vesicle called a vesosome. A vesosome is a large liposome that contains smaller liposomes, smaller emulsions particles or smaller solid particles. The method of producing a vesosome is to first make very small liposomes of the surfactant chemistry desired for the vesosome outer surface. Then addition of ethanol (EtOH) unfolds the liposomes into sheets. The ethanol is removed by centrifugation or dialysis, and yet the lipids remain in stable sheets as long as the temperature is kept sufficiently cool. At this point a suspension of small liposomes or an emulsion or a suspension of solid nanoparticles can be stirred into the suspension of lipid sheet. Drugs, DNA, fluorescent molecules or targeting molecules can also be mixed in with the sheets. Then the mixture is heated and the lipid sheets refold into spherical vesicles, trapping the emulsion, liposomes, nanoparticles, drugs or other molecules inside the reformed liposomes. [E. T. Kisak, B. Coldren, C. A. Evans, C. Boyer, and J. A. Zasadzinski (2004) "The vesosome—A multicompartment drug delivery vehicle," *Current Medicinal Chemistry*, 11, 199-219.] In the case of an emulsion trapped inside, an eLiposome is formed. Reported vesosome formulations include bilayer components of dipalmitoylphosphatidylcholine (DPPC), disteroylphosphatidylcholine (DSPC), cholesterol (Ch) in small amounts, and PEG-2000-DPPE (2000Da-polyethyleneglycol-dipalmitoylphosphatidylethanolamine).

Another method of forming an eLiposome is to coat the liposomal surfactants on the surface of a glass vessel and then add a stable emulsion to the vessel. The vessel is gently swirled for many minutes at a warm temperature as the liposome surfactants come off the glass and form liposomes with the emulsion trapped inside. The eLiposomes can be reduced in size to a smaller diameter by passing through a filter membrane with the appropriate sized holes, such as a 0.2 μm polycarbonate filter membrane. Emulsion droplets on the outside of eLiposomes can be ignored or can be removed by separation techniques such as density gradients, commonly known in the art.

An example of an eLiposome that possesses many of the embodiments described herein is illustrated schematically in FIG. 1. The outer bilayer membrane of the eLiposome is composed of phospholipids [40]. This bilayer also incorporates phospholipids attached to PEG chains [10], and PEG chains [30] that present targeting moieties [20] for specific targeting. Within the eLiposome are nanoemulsions [70] stabilized by surfactants [60]. This schematic also shows DNA molecules [50] as a therapeutic payload. This schematic is not meant to be shown to scale, and is only illustrative of one of many possible embodiments, and is not limiting in any way.

Externalized Emulsions

Another approach is to attach the phase-changing emulsion particles to the outside of formed liposomes. This can be done by several methods. For example, the emulsion could be formed with anionic surfactants and the liposome with cationic surfactants, or vice versa. When mixed together, the two vesicles will be electrostatically attracted to each other, and the small emulsion particles will decorate the exterior of the liposomes. Another approach uses the specific non-covalent interaction of two molecules to link the emulsions to the liposomes. Examples include antigen-antibody interactions, in which the antibody is attached to one vesicle, and the antigen to another. Biotin-streptavidin is another interacting pair that could be used similarly. It is also possible to covalently link the emulsion particles to the liposome by employing organic chemistry techniques such as condensation reactions, transesterification, transamidation, click chemistry techniques, and other synthetic techniques known in the art.

Expansion for Rupture of Liposomes and Endosomes

As provided herein, nano-sized emulsions of light perfluorocarbons can be contained within an eLiposome that can extravasate into tumors by the EPR effect, where they can be activated by ultrasound to release drug or DNA from liposomes, and to rupture endosomes, thus spilling the contents of the liposome into the cytosol of the targeted cell.

Lipid bilayers can sustain only about 3% area expansion before they rupture. In general, as a liquid expands into a vapor, there may be up to about a 1,000-fold increase in volume, such as liquid water boiling to water vapor. The exact expansion depends on the temperature and pressure of the gas phase. The light perfluorocarbons of the technology herein have very high vapor pressure, so at body temperature, this expansion ratio is approximately 103 for PFC5 and 259 for PFC6. Assuming a 100-fold expansion, for a liposome of 500 nm diameter, and a 100-nm-diameter emulsion droplet, only 1 nanoemulsion particle is required to burst the liposome; more specifically only 0.6% of the PFC liquid in that droplet need vaporize to reach the 3% area expansion threshold for liposome lysis.

Considering an endosome of 1-micron diameter—larger than average—and assuming that no excess endosome membrane is stored in folds or invaginations, only 1 emulsion nanodroplet, only 50% vaporized, is needed to rupture the endosome membrane. If there were folds present giving a nominal area expansion of 30%, then vaporization of 5 nanoemulsion particles would be required. Fewer particles would be required in a smaller endosome.

There are some reports of general interactions of PFC emulsions with high frequency low power ultrasound [T. Giesecke and K. Hynynen (2003) "Ultrasound-mediated cavitation thresholds of liquid perfluorocarbon droplets in vitro," *Ultrasound in Medicine and Biology*, 29, 1359-1365; O. Couture, P. D. Bevan, E. Cherin, K. Cheung, P. N. Burns, and F. S. Foster (2006) "Investigating perfluorohexane particles with high-frequency ultrasound," *Ultrasound in Medicine and Biology*, 32, 73-82; N. R. Soman, J. N. Marsh, M. S. Hughes, G. M. Lanza, and S. A. Wickline (2006) "Acoustic activation of targeted liquid perfluorocarbon nanoparticles does not compromise endothelial integrity," *Ieee Transactions on Nanobioscience*, 5, 69-75.]. Miller et al have used liquid perfluorocarbon droplets much larger than 1 micron in studies of gene transfection using a shock wave from lithotripsy technology. [D. L. Miller and J. M. Song (2002) "Lithotripter shock waves with cavitation nucleation agents produce tumor growth reduction and gene transfer in vivo," *Ultrasound in Medicine and Biology*, 28, 1343-1348.] The shock wave transformed these large liquid drops into even larger gas bubbles that enhanced gene transfection. The initial liquid droplet size and resulting gas bubbles in Miller's work were too large to pass through endothelial gaps and fenestrations. Rapoport et al made micelles and nanoemulsions of PFC5 stabilized with biodegradable block copolymers, and used these to deliver doxorubicin in vitro and in vivo [N. Rapoport, Z. G. Gao, and A. Kennedy (2007) "Multifunctional nanoparticles for combining ultrasonic tumor imaging and targeted chemotherapy," *Journal of the National Cancer Institute*, 99, 1095-1106]. None of these previous studies employed eLiposomes or delivered therapeutics through an endosomal pathway.

Timing and Location

The use of ultrasound targets therapy to specific locations in the body. This technique can also be applied in vitro for gene transfer to a plate of cultured cells. Ultrasound can be focused at the desired delivery site in the body. Drug that remained captured in intact endosomes would be digested and rendered inactive and perhaps excreted. Therefore, even if the therapeutic carrier, targeted or not, is distributed through the body, the use of ultrasound as a triggering modality ensures that the drug will be released only at the desired site, thus eliminating drug or gene release in other tissue, a potential source of many side-effects of chemotherapy.

For controlled timing ultrasound can be turned on and turned off precisely by the flip of a switch or by other machine control. The timing of release can be carefully controlled to achieve the desired accumulation of the therapeutic in the targeted tissue. Endosomes containing liposomes with phase changing emulsions may be burst by ultrasound at the desired location and desired time. Furthermore, ultrasonic irradiation (insonation) may be applied non-invasively to nearly all tissues in the body except within lungs and bones.

Non-Toxic Materials

The technology provided herein avoids the use of lytic lipids, proteins, ionic polymers, and extreme osmotic imbalances currently used in endosomal delivery techniques. The non-toxic perfluorocarbon molecules, already FDA approved for other in vivo technologies, will be easily eliminated by exhalation. The surfactants of some embodiments are phospholipids and cholesterol, sometimes with short-chain perfluorocarbon polyethers, which are non-toxic and small enough to be cleared by the kidneys.

Targeting Molecules

In some embodiments liposomes have targeting molecules ligated to their surface for active targeting to specific tissues. In certain embodiments the targeting molecules are attached to the liposomes via by polyethyleneglycol (PEG) spacer chains to molecules incorporated into the liposomal bilayer.

Ultrasound can be used to release the therapeutic into the cytosol at the desired time and location after the targeting vesicles have collected in the tissue. In some embodiments a targeting molecule is a biomolecule or a fragment of a biomolecule including without limitation proteins, polypeptides, antibodies, poly nucleic acids, DNA, RNA, carbohydrates, biotin, avidin and vitamins. A targeting molecule may sometimes be a folate molecule or a derivative of folic acid.

Site Specific Chemotherapy in Vivo

A key requirement of targeted drug delivery is the ability to deliver to only one tissue or one site in the body. In certain embodiments a radiation-triggered targeting technique like ultrasound, electric fields, magnetic fields, heat or light (laser) is used to effect a process at the desired site that allows a delivery vehicle to be activated only in the radiated tissue.

In one technique ultrasound may be focused on the target site through intervening tissue. In some embodiments ultrasound is used to expand the phase transforming liquid within prepared liposomes and spill the therapeutic contents of the liposome into the cellular cytosol. In certain embodiments the ultrasound delivers heat and thereby activates heat sensitive liposomes or thermally responsive polymers that carry the therapeutics, or create hyperthermia that enhances the action of conventional therapies. Ultrasound may sometimes excite gas bubbles in the targeted area and cause them to collapse, producing shear stress on vesicles and cells in the immediate vicinity of the excited bubble.

In certain embodiments targeting moieties (ligands) are attached to the prepared liposome, which is allowed to circulate in the body until it reaches and attaches to the desired target. In some embodiments attachment of antibodies is done by covalent attachment via the available —SH groups in Fab fragments of specific antibodies. In some embodiments attachment of antibodies is done by covalent attachment via carbodiimides or maleimides.

In some embodiments particles are allowed to accumulate passively in a tumor by the EPR effect, which is described as follows. In normal tissues, the endothelial cells lining the capillaries have sufficiently tight junctions that only particles with sizes<5 nm can pass. However, the endothelial lining of tumors is often compromised and has much larger gaps. As blood flows through the tumor vasculature, vascular pressure pushes plasma and its larger components through the gaps and fenestrations that occur abundantly, thus delivering vesicles including therapeutic carriers into the extravascular compartment beyond the endothelium. The narrower spaces in the extravascular compartment trap the larger particles that have entered and then retain them in the tumor tissue. The reduced lymphatic drainage of tumors further enhances this entrapment effect. This concentration of particles within tumors with hyperpermeable vasculature is known as the enhanced permeation and retention effect, or the EPR effect. Measurable accumulation is evident 30 minutes post administration, and accretion may continue for hours.

Many types of tumors exhibit the EPR effect such that nanosized vesicles extravasate and collect in the tissue beyond the capillaries. Micelles, liposomes and "solid" particles of nanometer size are known to extravasate. The concentration in the tissue builds up with time after injection, and often reaches a maximum from 48 to 72 hours after injection, depending on the tumor and the vesicle size. In some embodiments such passive targeting is combined with ultrasonic disruptions of liposomes and endosomes to release the therapeutic contents.

Ultrasonic Gene Delivery In Vitro

Gene delivery technology is usually divided into the use of viral and non-viral vectors. While viral vectors have displayed high efficiency in transfection, several safety concerns limit their use, including poor specific targeting, hepatic toxicity, immunogenicity and the high cost of producing large amounts of pure virus. Non-viral vectors include polysaccharides (e.g. Chitosan), liposome carriers, gas bubbles and cationic polymers. Their advantages include low cost of large-scale production, ease of use, and low immunogenicity. Their main disadvantage lies in their poor transfection efficiency.

Several strategies are used to produce non-viral transfection, including electroporation, ultrasonication, or direct injection using a gene gun.

Ultrasound-mediated gene transfection in vitro is known in the art using genes for protein markers such as green fluorescent protein (GFP), luciferase, and β-galactosidase. These techniques sometimes employ microbubbles filled with perfluorocarbon gases or sulfur hexafluoride.

DNA or plasmids bound to contrast agent bubbles have been injected into the general circulation and then ultrasound was focused only on one tissue or organ. Reports have shown gene transfection to the targeted heart, pancreas, and skeletal muscle, but little, if any transfection in the non-targeted adjacent tissues, even though similarly exposed to the gene carrier, but without ultrasound. Most of these were reporter genes such as GFP.

In certain embodiments herein, in vitro gene transfection uses nanoemulsions in liposomes configured for endocytosis and low pressure, including ultrasound, to deliver genes from the endosomes.

Formulation and Delivery

This technology can be applied for delivery of drugs that are at least slightly soluble in water and that do not cross a lipid bilayer, so they can be sequestered inside the liposome. This includes chemotherapeutics such as doxorubicin and other anthracyclines. DNA and RNA (including siRNA) can be sequestered inside the liposome and then released at the desired time and location into the cytosol either free or associated with the appropriate nuclear localization molecules. Applications include cancer therapy, controlled drug release in pain control, marker delivery and anti-inflammatory delivery as well as in vitro gene delivery to cell cultures, and signal or drug delivery to in vitro engineered tissues.

Liposomes may be formulated for delivery including with a pharmaceutically acceptable carrier, or compound. As used herein, the term "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include parenteral, e.g., intravenous, intradermal, subcutaneous, oral (e.g., inhalation), transdermal (topical), transmucosal, nasal, optical, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, other fluids configured to preserve the integrity of the liposome, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, isotonic agents, for example, sugars, polyalcohols such as mannitol, sorbitol, and sodium chloride sometimes are included in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means, including nasal and optical. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. Delivery vehicles can also be prepared in the form of suppositories (e.g., with conventional suppository bases such as cocoa butter and other glycerides) or retention enemas for rectal delivery.

In some embodiments oral or parenteral compositions are formulated in a dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Molecules which exhibit high therapeutic indices often are utilized. While molecules that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such molecules often lies within a range of circulating concentrations that include the $ED_{50}$ with little or no toxicity. The dosage may vary within this range depending upon the dosage form employed and the route of administration utilized. For any molecules used in the methods described herein, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. Another example of effective dose determination for an individual is the ability to directly assay levels of "free" and "bound" compound in the serum of the test subject. Such assays may utilize antibody mimics and/or biosensors.

Antibody conjugates can be used for modifying a given biological response, the drug moiety delivered to the cell cytosol is not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin, or *diphtheria* toxin; a polypeptide such as tumor necrosis factor, .alpha.-interferon, .beta.-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors. Alternatively, an antibody can be conjugated to a second antibody to form an antibody heteroconjugate.

For compounds, exemplary doses include milligram or microgram amounts of the compound per kilogram of subject or sample weight, for example, about 1 microgram per kilogram to about 500 milligrams per kilogram, about 100 micrograms per kilogram to about 5 milligrams per kilogram, or about 1 microgram per kilogram to about 50 micrograms per kilogram. It is understood that appropriate doses of a small molecule depend upon the potency of the small molecule with respect to the expression or activity to be modulated, particularly when one delivers the molecule directly to the cell cytosol. When one or more of these small molecules is to be administered to an animal (e.g., a human) in order to modulate expression or activity of a polypeptide or nucleic acid described herein, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

Nucleic acid molecules can be inserted into liposomes and used in gene therapy methods for treatment, including without limitation, cancer. Gene therapy liposomes can be delivered to a subject by, for example, intravenous injection and local administration. Pharmaceutical preparations of gene therapy liposomes can include a gene therapy liposome in an acceptable diluent, or can comprise a slow release matrix in which the gene delivery vehicle is imbedded.

Pharmaceutical compositions can be included in a container, pack, or dispenser together with instructions for administration.

Pharmaceutical compositions of active ingredients can be administered by any of the paths described herein for therapeutic and prophylactic methods for treatment. With regard to both prophylactic and therapeutic methods of treatment, such treatments may be specifically tailored or modified, based on knowledge obtained from pharmacogenomic analyses described herein. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes, oligonucleotides, and analgesics.

Successful treatment of disorders including cancer can be brought about by techniques that serve to inhibit the expression or activity of target gene products Inhibitory molecules can include, but are not limited to peptides, phosphopeptides, small organic or inorganic molecules, or antibodies (including, for example, polyclonal, monoclonal, humanized, anti-idiotypic, chimeric or single chain antibodies, and FAb, F(ab')2 and FAb expression library fragments, scFV molecules, and epitope-binding fragments thereof).

Further, antisense and ribozyme molecules that inhibit expression of the target gene can also be used to reduce the level of target gene expression, thus effectively reducing the level of target gene activity. Still further, triple helix molecules can be utilized in reducing the level of target gene activity.

It is possible that the use of antisense, ribozyme, and/or triple helix molecules to reduce or inhibit mutant gene expression can also reduce or inhibit the transcription (triple helix) and/or translation (antisense, ribozyme) of mRNA produced by normal target gene alleles, such that the concentration of normal target gene product present can be lower than is necessary for a normal phenotype. In such cases, nucleic acid molecules that encode and express target gene polypeptides exhibiting normal target gene activity can be introduced into cells via the liposome gene therapy method herein.

Another method by which nucleic acid molecules may be utilized in treating or preventing a disease characterized by aberrant gene expression is through the use of aptamer molecules specific for the defective polypeptide. Aptamers are nucleic acid molecules having a tertiary structure that permits them to specifically bind to polypeptide ligands. Since nucleic acid molecules may in many cases be more conveniently introduced into target cells than therapeutic polypeptide molecules may be, aptamers offer a method by which abnormal polypeptide activity may be specifically decreased without the introduction of drugs or other molecules which may have pluripotent effects.

Antibodies can be generated that are both specific for target gene product and that reduce target gene product activity. Such antibodies may, therefore, by administered in instances whereby negative modulatory techniques are appropriate for the treatment of cancer and related disorders.

In instances where the target antigen is intracellular and whole antibodies are used, liposomes can be used to deliver the antibody or a fragment of the Fab region that binds to the target antigen into cells. Where fragments of the antibody are used, the smallest inhibitory fragment that binds to the target antigen often is utilized. For example, peptides having an amino acid sequence corresponding to the Fv region of the antibody can be used. Alternatively, single chain neutralizing antibodies that bind to intracellular target antigens can also be administered. Such single chain antibodies can be administered, for example, by expressing nucleotide sequences encoding single-chain antibodies within the target cell population.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided. One skilled in the relevant art will recognize, however, that the invention can be practiced without one or more of the specific details, or with other methods, components, materials, and so forth. In other instances, structures, materials, or operations that are known in the art are not shown or described in detail to avoid obscuring aspects of the invention.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

EXAMPLES

Example 1

Emulsion, PFC6, Zonyl

Stable perfluorohexane (PFC6) emulsions were formed as follows. Zonyl FSO (DuPont) fluorocarbon surfactant was mixed with distilled deionized water (ddH2O) to form a 0.5 mg/mL stock solution. Then 0.2 g of Zonyl stock solution and 0.2 g of PFC6 were added to 3 mL of ddH2O in a glass vial. The vial was cooled in an ice bath and then sonicated for about one minute with a 20-kHz ultrasound probe (VCX750, 3 mm probe, Sonics and Materials, Newton, Conn.) at 20% power, or until the perfluorocarbon phase was suspended. The sample was allowed to sit for 1 minute and then sonicated again for 1 minute. This cycle was repeated a final time with a 3-minute sonication. The resulting emulsion typically had droplets from 150-200 nm as measured by dynamic light scattering (DLS) using a Brookhaven 90Plus Particle Sizer (Brookhaven Instruments Co., Holtsville, N.Y.).

Example 2

Emulsion, PFC6, DPPC

Perfluorohexane (PFC6) emulsions were stabilized with dipalmitoylphosphatidylcholine (DPPC). 10 mg of DPPC (from a 30 mg/mL stock solution of DPPC in ddH2O) and 0.1 g of PFC6 were added to 1.5 mL total volume of ddH2O. The sample was cooled in an ice bath and then sonicated for one minute with a 20-kHz ultrasound probe (VCX750, 3 mm probe, Sonics and Materials, Newton, Conn.) at 20% power until the perfluorocarbon phase was suspended. The sample was allowed to sit for 1 minute and then sonicated again. The resulting emulsion typically had droplets from 200-400 nm. Droplet size was reduced by extrusion at 45° C. through a 100-nm or 50-nm polycarbonate filter using an Avanti Mini Extruder. The size distributions of the resulting emulsion droplets were centered at 85 or 40 nm, respectively, as measured by DLS.

Example 3

Emulsion, PFC6, DPPA 20 mg of dipalmitoyl-sn-glycero-3-phosphate (DPPA) were placed in a clean 2 mL vial. Then 1 mL of warm ddH2O (45° C.) was added and the vial capped and shaken by hand until the DPPA was dispersed. The cap was removed and the bubbles allowed to break up. Then 0.185 g of PFC6 was added to the vial. A very small Teflon-coated stir bar was added, and the vial was filled to the top with more warm ddH2O. The vial was placed underwater in a basin of warm ddH2O, and a clean cap with rubber septum was placed underwater and all attached air bubbles removed. The cap was placed on the vial underwater so no bubbles were introduced into the vial. The cap was crimped in place underwater with a hand crimper. The vial was examined, and if any bubbles were found, the sample was discarded. Then the vial containing the stir bar was heated at 44° C. for 4 hours and then immediately inserted into a dental amalgamator. It was shaken for 30 seconds, left stationary for 30 seconds, and this process repeated twice more. The resulting emulsion droplets had a size distribution from 100 to 220 nm.

Example 4

Emulsion, PFC5, DMPC

Perfluoropentane (PFC5) was stored in a freezer at −20° C. ddH2O was kept in a refrigerator at 4° C. First 0.067 g of dimyristoylphosphatidylcholine (DMPC) was placed into a clean 2 mL vial. Then 1 mL of warm ddH2O (45° C.) was added and the sample was agitated until the DMPC was dispersed. Then the sample was cooled on ice. Next 0.185 g of cold PFC5 was added to the vial. A very small Teflon-coated stir bar was added, and the vial filled to the top with more cold ddH2O. The vial was placed underwater in a basin of cold (4° C.) ddH2O, and a clean cap with rubber septum was placed underwater and all attached air bubbles removed. The cap was placed on the vial underwater so no bubbles were introduced into the vial. The cap was crimped in place underwater with a hand crimper. The vial was examined, and if any bubbles were found, the sample was discarded. Then the vial containing the stir bar was inserted into a dental amalgamator. It was shaken for 30 seconds, left stationary for 30 seconds, and this process was repeated twice more. The resulting emulsion droplets had a size distribution from 100 to 250 nm.

Example 5

Emulsion, PFC5, DPPA

Perfluoropentane (PFC5) was stored in a freezer at −20° C. ddH2O was kept in a refrigerator at 4° C. 20 mg of dipalmitoyl-sn-glycero-3-phosphate (DPPA) were placed into a clean 2 mL vial. Then 1 mL of room temperature ddH2O (20° C.) was added and the vial capped and shaken by hand until the DPPA was dispersed. The cap was removed and the bubbles allowed to break up. The container was cooled on ice and 0.185 g of cold PFC5 was added to the vial. A very small Teflon-coated stir bar was added, and the vial filled to the top with more cold ddH2O. The vial was placed underwater in a basin of cold (4° C.) ddH2O, and a clean cap with rubber septum was placed underwater and all attached air bubbles removed. The cap was placed on the vial underwater so no bubbles were introduced into the vial. The cap was crimped in place underwater with a hand crimper. The vial was examined, and if any bubbles were found, the sample was discarded. Then the vial containing the stir bar was inserted into a dental amalgamator. It was shaken for 30 seconds, left stationary for 30 seconds, and this process repeated twice more. The resulting emulsion droplets were from 100 to 250 nm. The emulsion was stored at 4° C. until use.

Example 6

Vesosome by Centrifugation Filled with Calcein, Including Separation

DPPC liposomes were prepared using a standard film hydration technique. DPPC was dissolved in chloroform and added to a round bottom flask. The solvent was removed under vacuum with a rotovap, leaving a thin dry lipid film on the flask. This film was hydrated by adding an aqueous solution (ddH2O, phosphate buffered saline or PBS) to the flask to a total lipid concentration of 30 mg/mL and heating the mixture to 60° C. while rotating for 30 minutes or until the majority of the lipid was suspended. When necessary, the flask was placed in a sonicating bath (Sonicor SC 100) to remove any remaining lipid residue from the flask. To form small unilamellar vesicles (SUVs), this hydrated solution was then either extruded through a 0.05 um filter while heating to 50° C. with an Avanti Mini Extruder or sonicated with a 20 kHz sonicating probe (VCX750, 3 mm probe, Sonics and Materials, Newton CT) for 15 minutes at 1.5 W/cm2. The resulting vesicles were measured to be 30 to 80 nm in diameter by DLS.

Interdigitated DPPC sheets were formed by adding ethanol dropwise while stirring to a total concentration of 3M. As the ethanol was added, the solution became more opaque white and showed an increase in viscosity. Once the sheets were formed excess ethanol was removed by centrifugation. The ethanol rich sheet suspension was centrifuged for 3 minutes at 3000 rpm at room temperature. The ethanol rich supernatant was removed and the pellet was redispersed in ddH2O, saline or PBS. The process was repeated, with the resulting sheet solution having an ethanol concentration less than 10 mM. This interdigitated sheet phase remained stable for several weeks as long as the temperature was maintained below the transition temperature (Tm) for DPPC (41° C.).

Calcein was encapsulated inside of the vesosomes by adding a concentrated calcein solution to the sheets. This solution was re-pipetted until well-mixed followed by several seconds of vortexing to ensure mixing. Then the suspension was heated to 50° C. and stirred for 30 minutes, allowing the sheets to fold around the adjacent calcein solution. The resulting vesicles had an average size greater than 1 µm. The vesosomes were reduced in size by extrusion through a polycarbonate filter with an Avanti Mini Extruder at 50° C. The resulting vesicles were 500-800 nm. The calcein external to the vesosomes was removed with a sephadex-25 spin column. The column was prepped by adding 2-3 mL of PBS and was spun for 2 minutes at 1000 rpm. The sample was then loaded onto the column, and was spun for 2 minutes at 1000 rpm.

Example 7

Vesosome by Dialysis Filled with Calcein, Including Separation

DPPC liposomes were prepared using a standard film hydration technique described in Example 6. Interdigitated DPPC sheets were formed by adding ethanol dropwise while stirring to a total concentration of 3M. As the ethanol was added, the solution became more opaque white and showed an increase in viscosity. Once the sheets were formed excess ethanol was removed by dialysis. The sheets were placed in a dialysis bag with a 3,500 MWCO and dialyzed against ddH2O for one to two hours; then the water was replaced with new ddH2O then allowed to dialyze overnight. After removal of the ethanol, concentrated calcein solution (usually 1 to 10 mM, depending upon the subsequent experiment) was added to the sheets and the suspension was heated to 50° C. for one hour to form liposomes. Unencapsulated calcein was removed on PD-10 desalting columns (GE).

Example 8

PFC6 eLiposome by Combining Examples 6 and 2, Including Density Cushion Separation DPPC liposomes were prepared using a standard film hydration technique as in Example 6. Interdigitated DPPC sheets were formed as in Example 6.

The eLiposomes were formed by adding 0.1-0.2 mL of emulsion suspension from Example 2 to the interdigitated sheets along with 0.1-0.2 mL of either ddH2O, PBS, saline or concentrated calcein solution. The appropriate amount of emulsion was added to encapsulate about 4 nanoemulsion droplets per eLiposome. The sheets were then heated to 50° C. and stirred for 30 minutes, allowing the sheets to fold around the adjacent aqueous solution, including emulsion droplets. The resulting vesicles had an average size greater than 1 µm. The eLiposomes were reduced in size by extrusion through polycarbonate filter with an Avanti Mini Extruder at 50° C. The resulting eLiposome vesicles were 500-800 nm as determined by DLS.

The calcein external to the vesosomes was removed as in Example 6. Finally the emulsion droplets external to the eLiposomes were removed by a density cushion separation as follows. 1 mL of sodium chloride of 300 mM (density of 1.01 gm/mL) was carefully injected into the bottom of a 3 mL plastic microfuge tube using a long thin Pasteur pipette. Then the more dense solution of 500 mM sucrose (density of 1.07 gm/mL) was slowly injected into the bottom of the tube under the sodium chloride. The eLiposome sample was carefully pipetted onto the top of the sodium chloride. The microfuge tube was spun at 2,000 rpm for 20 minutes in an Eppendorf 5451C microcentrifuge. The eLiposomes were collected from the cloudy interphase between the salt solution layer and the sucrose layer. A small liquid "pellet" of external emulsion collected at the very bottom of the microfuge tube. Collection of eLiposomes at the interphase occurred because the average density of eLiposomes was greater than that of the sodium chloride solution, but less than the density of the sucrose solution; furthermore the density of the external emulsion particles was greater than the sucrose solution density, so they spun all the way to the bottom. Empty vesosomes floated to the top of the salt phase. The eLiposomes collected from the interphase region had peaks at about 100 and 500 nm, assigned to internal emulsion droplets and to the outer liposome membrane, respectively. The top sodium chloride phase had a peak centered at about 400 nm, assigned to empty liposome vesicles.

Example 9

DMPC/PFC6/DPPA eLiposome by Film Hydration Using Example 3, Including Density Cushion Separation DMPC dissolved in chloroform was dried on the sides of a 50-mL round bottom flask in a rotovap, depositing about 6 mg DMPC. Then 1.5 mL of the DPPA emulsion of PFC6 of Example 3 with a size of about 130 nm was added to the flask, and the flask was rotated in the rotovap without vacuum in a 45° C. water bath for 40 minutes. The resulting suspension contained eLiposomes as indicated by DLS. There was a peak at about 165 nm assigned to the emulsion and a peak at 450 nm assigned to the eLiposome vesicles. The emulsions external to the eLiposomes were removed by the density cushion technique as taught in Example 8.

Example 10

DMPC/PFC5/DPPA eLiposome by Film Hydration using Example 5, Including Density Cushion Separation DMPC dissolved in chloroform was dried on the sides of a 50-mL round bottom flask in a rotovap, depositing about 6 mg DMPC. Then 1.5 mL of the cold PFC5/DPPA emulsion of Example 5 with a size of about 130 nm was added to the flask. The flask was pressurized to 0.1 MPa under an Ar atmosphere and heated to 45° C. with swirling for 30 to 40 minutes. Then the flask was cooled on ice under pressure. After cooling the pressure was reduced and the sample removed and stored in the refrigerator at 4° C.

The resulting suspension contained eLiposomes as indicated by DLS. There was a peak at about 160 nm assigned to the emulsion and a peak at 460 nm assigned to the eLiposome vesicles. The emulsion droplets external to the eLiposomes were removed by the density cushion technique as taught in Example 8.

Example 11

Preparation of PE-PEG-Folate

Folate was attached to the distal end of a PEG chain as a targeting moiety. First 66 mg DSPE-PEG2000-amine (Avanti) was placed in a round bottom flask. Then a 20% molar excess of folic acid in anhydrous dimethyl sulfoxide (DMSO) was added. One-third by volume pyridine was added to the round bottom flask. N,N'-dicyclohexylcarbodiimide (DCC) was then added to the mixture, and it was left to react for 4 hours at room temperature in the dark. The pyridine was removed by evaporation using a rotovap. Double distilled water was then added to make a mixture of 90% water by volume. The unreacted folic acid, DCC, byproducts, and DMSO were then removed by dialyzing the mixture using a dialysis bag with a 3500 molecular weight cut-off. Other non-soluble byproducts were removed by centrifugation. NMR confirmed attachment of the folic acid to the PEG chain.

Example 12

Insertion of PE-PEG-Folate into eLiposome of Example 8

Some eLiposomes containing PFC5 emulsions were prepared as described in Example 5 by hydrating the phospholipids under pressure. After hydration the eLiposome mixture was placed on ice to prevent evaporation of the PFC5. DSPE-PEG-folate micelles were prepared by dissolving 2 mg of DSPE-PEG-folate (Example 11) in 0.6 mL of DMSO, and then adding 5.4 mL of ddH2O. The DMSO was removed by dialysis in a 3500 MWCO bag. The resulting DSPE-PEG-folate micelles were then mixed with the eLiposome formulation in a round bottom flask then pressurized with Ar to 0.1 MPa gauge pressure. The mix was incubated with swirling at 45° C. for two hours under pressure. It was then cooled on ice under pressure before the sample was removed. Dynamic light scattering results showed that the sizes of the eLiposomes and the emulsions within were unchanged by this insertion procedure, and that the DLS peak corresponding to the DSPE-PEG-folate micelles had disappeared.

Example 13

Insertion of PE-PEG into Vesosomes Filled with Calcein

To impart stealth character to vesosomes, insertion of polyethyleneglycol (PEG) chains was done by two methods. In the first method the DSPE-PEG2000 (PEG of 2,000 molecular weight, Avanti) was added to DPPC at 3 and 5 mole % in chloroform and the mixture was dried on a round bottom flask. Then lipid sheets were formed from this mixture and mixed with concentrated calcein before reforming into vesosomes containing the DSPE-PEG2000 as described in Example 6. Unencapsulated calcein was dialyzed away using a 50,000 MWCO dialysis bag. Vesosome formation was confirmed by fluorometry in that adding Triton X to the solution produced a step change increase in the fluorescence, verifying formation of calcein-containing vesosomes with PEG incorporated into the bilayers.

The second method consisted of first forming vesosomes and then inserting the DSPE-PEG2000 in a subsequent step. First calcein-filled vesosomes were made by the method of Example 6 and unencapsulated calcein was dialyzed away using a 50,000 MWCO dialysis bag. Micellar solutions of DSPE-PEG2000 were made by dissolving it in DMSO and then hydrating with water to make a 10% by volume solution of DMSO. The DSPE-PEG2000 concentration was approximately 100 µM. The DMSO was dialyzed away with a dialysis bag of MWCO 3,500 three times against double-distilled water. These micelles were added to the calcein-filled vesosomes and incubating them at 50° C. for 1 hr. Formation of DPPC vesosomes containing DSPE-PEG-lipids was verified by dynamic light scattering results showing the disappearance of the smaller DSPE-PEG2000-micelle signal and an increase in size of the vesosome diameter. Adding Triton X to the solution produced a step change increase in the fluorescence, verifying formation of calcein-containing vesosomes with DSPE-PEG2000 incorporated into the lipid bilayers.

Example 14

Ultrasonic Release of Calcein from eLiposomes of Examples 6 and 8

Figure 2:
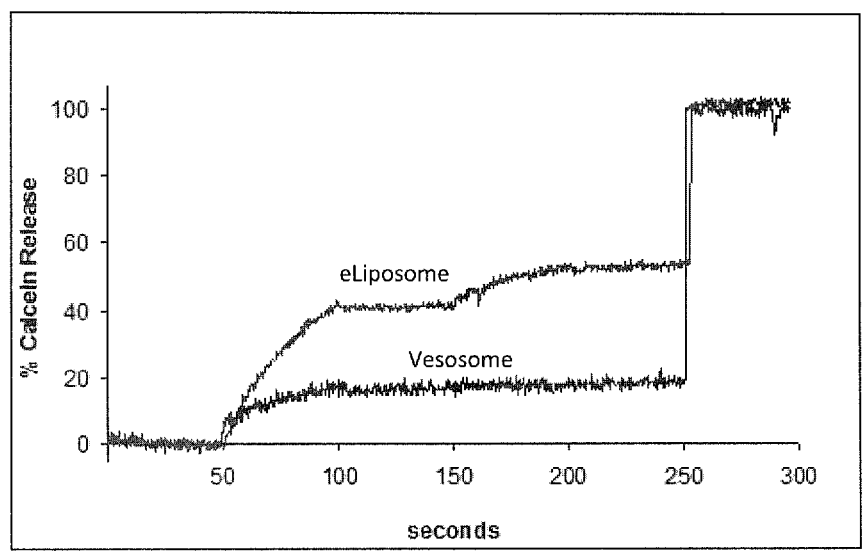
FIG. 2 depicts ultrasonic release of calcein from eLiposomes in accordance with the present technology, measured using a fluorometer. The eLiposomes showed a 100% greater release than the empty vesosomes. Time in seconds is shown on the x-axis, and the normalized fluorescence signal, proportional to the percentage of calcein released, is shown on the y-axis.

Ultrasonic release of calcein from eLiposomes was measured using a fluorometer. A 20-kHz ultrasonic probe (model VC130PB, Sonics & Materials Inc., Newtown, Conn.) was immersed approximately 0.2 cm in to a 2 mL sample in a cuvette through an opening in the lid of the fluorometer. Excitation and emission wavelengths were set at 488 and 525 nm, respectively. As self-quenched calcein was released from the vesicles, it became diluted (and unquenched) and a fluorescent signal could be detected. A baseline fluorescence signal was collected for 50 seconds, followed by 50 seconds of sonication at 1 W/cm2, followed by another 50 seconds with the probe turned off. Fluorescence was monitored continually. Finally, the detergent Triton X-100 (30 uL of 5 wt %) was added to the cuvette to destroy liposomes completely and another measurement was recorded that represented the fluorescence level of 100% release. This experiment was performed on eLiposomes prepared in Example 8, and on calcein-containing vesosomes formed by the sheet refolding technique of Example 6. The eLiposomes showed a 100% greater release compared to the empty vesosomes. A typical result is shown in FIG. 2; time in seconds is shown on the x-axis, and the normalized fluorescence signal, proportional to the percentage of calcein released, is shown on the y-axis.

Example 15

TEM by Negative Staining

Figure 3:
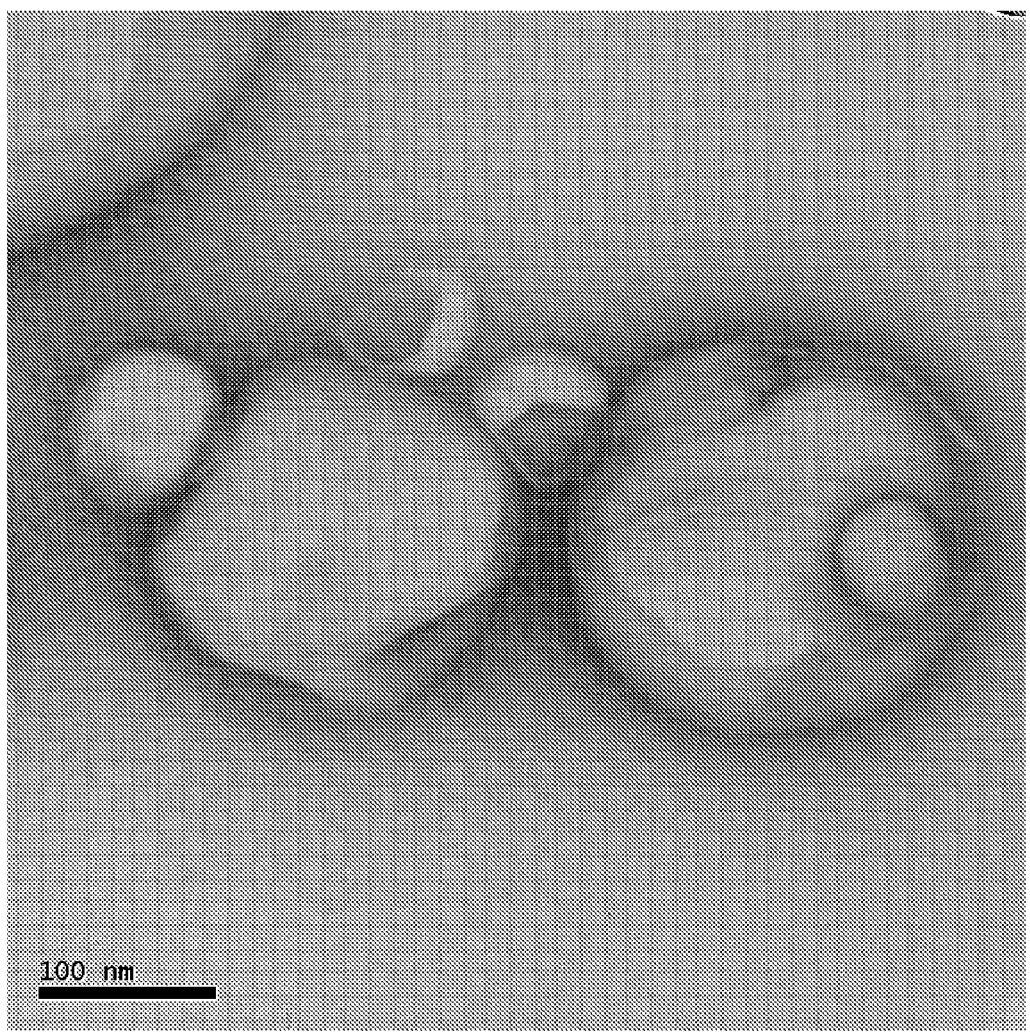
FIG. 3 depicts an example of vessels in accordance with the present invention visualized by electron microscopy. The larger vesicles are the eLiposomes, and the smaller vesicles are believed to be emulsion droplets external to the eLiposomes.

An eLiposome sample was prepared as in Example 8, but the external emulsion droplets were not separated so they could be visualized also. Samples were imaged by TEM using negative staining as follows. The sample was placed on a continuous carbon coated copper grid and allowed to settle for 20 seconds before being blotted away by filter paper. A uranyl acetate solution was then added to the grid for 20 seconds before it was blotted away. Images were recorded at 300 kV on an FEI Tecnai F30 transmission electron microscope (Hillsboro, Oreg., USA) using a Gatan 1024×1024 CCD camera. FIG. 3 is an example of vessels visualized by this process. The larger vesicles are the eLiposomes, and the smaller vesicles are believed to be emulsion droplets external to the eLiposomes. This technique cannot visualize emulsions within the eLiposome.

Example 16

CryoTEM of eLiposomes

Figure 4:
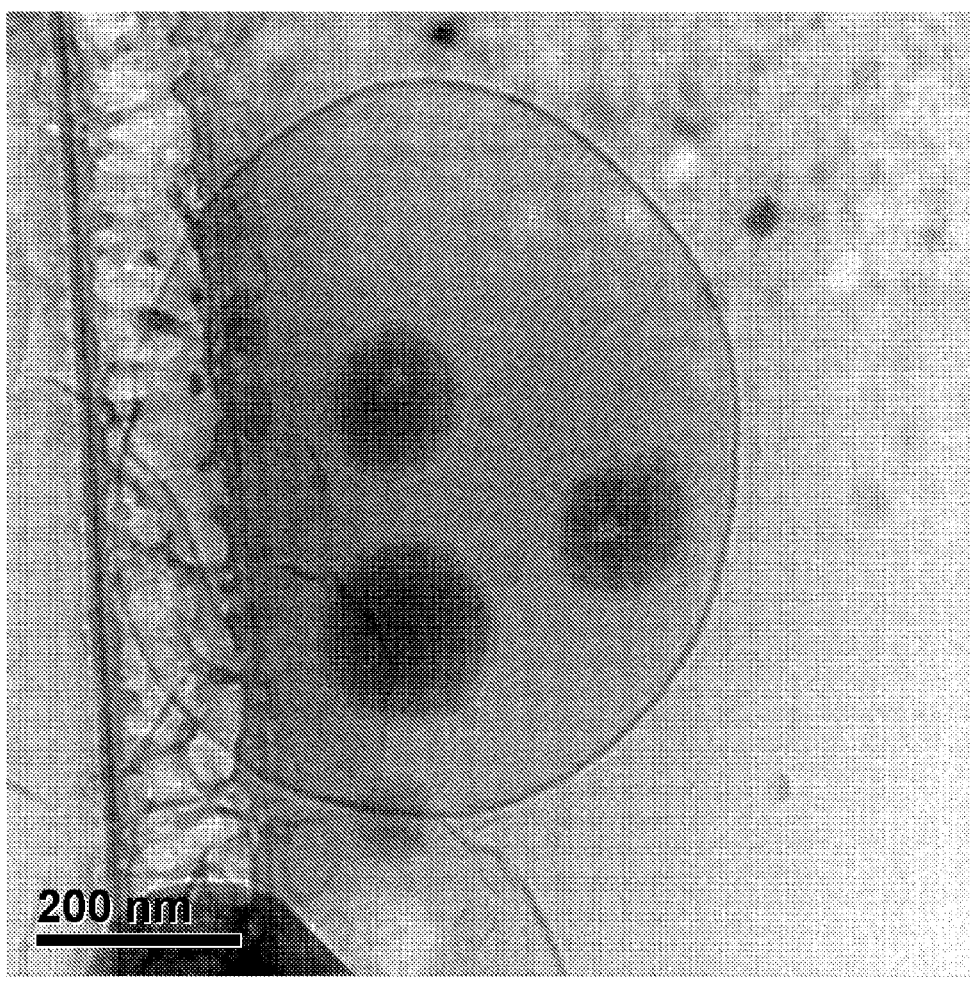
FIG. 4 depicts example of eLiposomes in accordance with the present technology visualized by electron microscopy. The large circular object is an eLiposome of about 600 nm×700 nm. There are 3 PFC6 emulsion droplets inside having diameters of about 133 nm, 164 nm and 111 nm. Rotation of the stage to plus 45° and minus 45° confirmed that the 3 emulsion droplets were inside the eLiposome, and not above or below it.

An eLiposome sample was prepared as in Example 8, but the external emulsion droplets were not separated so they could be visualized also. Samples were imaged by cryoTEM as follows. Several µl of sample suspension were placed on a holey-carbon-coated copper grid. The grid was then blotted with filter paper and plunge frozen in liquid ethane with an FEI Vitrobot (Hillsboro, Oreg., USA). Frozen grids were stored in liquid nitrogen until being transferred to a Gatan 626 cryoholder (Pleasanton, Calif., USA). Cryo-TEM images were recorded at 300 kV on an FEI Tecnai F30 transmission electron microscope (Hillsboro, Oreg., USA). To improve contrast, the objective lens was de-focused several micrometers. Images were recorded on a Gatan 1024×1024 CCD camera. FIG. 4 shows an example of eLiposomes that were visualized. The large circular object is an eLiposome of about 600 nm×700 nm. There are 3 PFC6 emulsion droplets inside having diameters of about 133 nm, 164 nm and 111 nm. Rotation of the stage to plus 45° and minus 45° confirmed that the 3 emulsion droplets were inside the eLiposome, and not above or below it.

REFERENCES

E. T. Kisak, B. Coldren, C. A. Evans, C. Boyer, and J. A. Zasadzinski (2004) "The vesosome—A multicompartment drug delivery vehicle," *Current Medicinal Chemistry*, 11, 199-219.

T. Giesecke and K. Hynynen (2003) "Ultrasound-mediated cavitation thresholds of liquid perfluorocarbon droplets in vitro," *Ultrasound in Medicine and Biology*, 29, 1359-1365.

O. Couture, P. D. Bevan, E. Cherin, K. Cheung, P. N. Burns, and F. S. Foster (2006) "Investigating perfluorohexane particles with high-frequency ultrasound," *Ultrasound in Medicine and Biology*, 32, 73-82.

N. R. Soman, J. N. Marsh, M. S. Hughes, G. M. Lanza, and S. A. Wickline (2006) "Acoustic activation of targeted liquid perfluorocarbon nanoparticles does not compromise endothelial integrity," *Ieee Transactions on Nanobioscience*, 5, 69-75.

D. L. Miller and J. M. Song (2002) "Lithotripter shock waves with cavitation nucleation agents produce tumor growth reduction and gene transfer in vivo," *Ultrasound in Medicine and Biology*, 28, 1343-1348.

N. Rapoport, Z. G. Gao, and A. Kennedy (2007) "Multifunctional nanoparticles for combining ultrasonic tumor imaging and targeted chemotherapy," *Journal of the National Cancer Institute*, 99, 1095-1106.

What is claimed is:

1. A composition comprising:
   a. a liposome configured to at least one of be taken into a cell, attach to a cell surface, and accumulate in a cell vicinity;
   b. a nanodroplet of a phase transforming liquid at least one of contained inside the liposome, within the liposome membrane, and attached to the exterior of the liposome, the phase transforming liquid being immiscible in water and the composition comprising a two phase aqueous/non-aqueous nanoemulsion, the phase transforming liquid having a vapor pressure capable of forming a gas at low pressure and the nanodroplet being configured to remain liquid above the normal boiling point of the phase transforming liquid and further configured to remain liquid after administration to a patient until activated by a decrease in pressure; and
   c. at least one functional molecule selected from the group consisting of a therapeutic molecule, a detectable label, and a targeting molecule, said functional molecule encapsulated by the liposome, within the lipid bilayer, or attached to the surface of the bilayer.

2. A composition according to claim 1 wherein the liposome is configured to be taken into the cell by at least one of endocytosis including pinocytosis and phagocytosis and merger with the cellular lipid bilayer.

3. A composition according to claim 1, wherein the amphipathic molecules are selected from the group consisting of cholesterols, phosphoglycerides, phospholipids, glycolipids, sphingomyelins, and PEGylated derivatives.

4. A composition according to claim 1, wherein the liposome is from about 50 to about 1,000 nanometers in diameter.

5. A composition according to claim 1, wherein the nanodroplet is from about 5 nm to about 900 nm.

6. A composition according to claim 1, wherein the phase transforming liquid is contained within the liposome.

7. A composition according to claim 1, wherein the phase transforming liquid is embedded in the liposomal bilayer.

8. A composition according to claim 1, wherein at least one of the phase transforming liquid and at least one of the surfactant used to stabilize the emulsion and the surfactant used to form the liposome is non-toxic.

9. A composition according to claim 1, wherein the phase transforming liquid contains at least one hydrocarbon molecule that forms a gas at low pressure.

10. A composition according to claim 1, wherein the phase transforming liquid contains at least one fluorocarbon molecule with a normal boiling temperature between −5° C. and 105° C.

11. A composition according to claim 1, wherein the phase transforming liquid contains at least one hydrofluorocarbon molecule with a normal boiling temperature between −5° C. and 105° C.

12. A composition according to claim 1, wherein the phase transforming liquid transforms to a gas upon decrease in pressure with a volume expansion of from at least 10 fold to at least about 1,000 fold.

13. A composition according to claim 1, wherein the phase transforming liquid comprises at least one nanodroplet stabilized by at least one amphipathic molecule.

14. A composition according to claim 1 wherein the targeting molecule is attached to the liposome by polyethyleneglycol (PEG) spacer chains to molecules incorporated into the liposomal bilayer.

15. A composition according to claim 1 wherein the targeting molecule is a biomolecule or a fragment of a biomolecule selected from the group consisting of proteins, polypeptides, antibodies, poly nucleic acids, DNA, RNA, carbohydrates, biotin, avidin, a folate molecule, and vitamins.

16. A composition according to claim 1 wherein the position of the therapeutic molecule is selected from the group consisting of contained within the liposome, contained within the bilayer forming the liposome, and attached to or associated with the surface of the liposome.

17. A composition according to claim 1 wherein the therapeutic molecule is at least one of a chemotherapeutic drug, pain relieving drug, anti-inflammatory drug, anti-arthritic drug, hormone, steroid, DNA, RNA, siRNA, poly nucleic acid, toxic molecule, cell signaling molecule, protein, enzyme and membrane permeabilizing molecule.

18. A composition according to claim 1 wherein the labeling molecule is at least one of a fluorescent molecule, light absorbing molecule, protein and enzyme.

19. A composition according to claim 1 wherein the nanodroplet is covalently bound to the surface of the liposome.

20. A composition according to claim 1 wherein the nanodroplet is attached to the exterior of the liposome by at least one of electrostatic attraction, non-covalent interaction, hydrophobic interactions, dispersion interaction and hydrogen bonding interaction.

\* \* \* \* \*